United States Patent
Bertolero et al.

(10) Patent No.: US 7,074,180 B2
(45) Date of Patent: Jul. 11, 2006

(54) VISUALIZATION DURING CLOSED-CHEST SURGERY

(75) Inventors: Arthur A. Bertolero, Danville, CA (US); Raymond S. Bertolero, Danville, CA (US); Jerome B. Riebman, Sunnyvale, CA (US)

(73) Assignee: Endoscopic Technologies, Inc., Danville, CA (US)

( * ) Notice: Subject to any disclaimer, the term of this patent is extended or adjusted under 35 U.S.C. 154(b) by 225 days.

(21) Appl. No.: 10/371,756

(22) Filed: Feb. 21, 2003

(65) Prior Publication Data

US 2003/0153810 A1 Aug. 14, 2003

Related U.S. Application Data

(63) Continuation of application No. 09/672,110, filed on Sep. 27, 2000, now abandoned, which is a continuation of application No. 09/171,206, filed as application No. PCT/US97/06112 on Apr. 10, 1997, now abandoned.

(60) Provisional application No. 60/014,922, filed on Apr. 10, 1996.

(51) Int. Cl.
*A61B 1/00* (2006.01)
*H04N 5/64* (2006.01)

(52) U.S. Cl. ............ 600/101; 600/112; 348/841; 206/438

(58) Field of Classification Search ............ 150/154, 150/165; 348/841, 818, 65; 206/438; 600/101, 600/102, 112, 109, 118, 122, 160, 194, 206; 128/849–854

See application file for complete search history.

(56) References Cited

U.S. PATENT DOCUMENTS 4,413,278 A * 11/1983 Feinbloom .................. 348/73

(Continued)

*Primary Examiner*—John P. Leubecker
(74) *Attorney, Agent, or Firm*—Gregory Scott Smith; Carol D. Titus; GSS Law Group

(57) ABSTRACT

An improvement in a method for closed-chest, video-assisted diagnostic or surgical treatment of a patient is provided. The improvement comprises draping a video monitor with a transparent sterile surgical drape and positioning the draped monitor within the surgical field so that a surgeon can perform an internal surgical or diagnostic procedure and view it on the monitor to provide improved visual alignment for the surgeon. A flexible, sterile drape for covering the video monitor is disclosed. An apparatus for assisting the surgeon in performing closed-chest, video-assisted surgical or diagnostic treatment of a patient is disclosed which comprises a movable cabinet having an adjustable arm to which is affixed a video monitor that can be extended into the surgical field of an operating room to improve the visualization of the surgery performed by the surgeon. An improved operating table for assisting a surgeon in performing closed-chest, video-assisted surgical or diagnostic treatment of a patient is also disclosed along with endoscopic visualization apparatus and an improved design of a view scope that allows the doctor to get closer to a patient during the operation.

27 Claims, 12 Drawing Sheets

U.S. PATENT DOCUMENTS

| | | | | |
|---|---|---|---|---|
| 4,948,154 A | * | 8/1990 | Guggenheim | 280/79.3 |
| 4,963,693 A | * | 10/1990 | Kodl | 174/11 R |
| 4,998,972 A | * | 3/1991 | Chin et al. | 600/109 |
| 5,032,913 A | * | 7/1991 | Hattori et al. | 348/70 |
| 5,080,155 A | * | 1/1992 | Crozier | 150/154 |
| 5,259,365 A | * | 11/1993 | Nishikori et al. | 600/102 |
| 5,297,538 A | * | 3/1994 | Daniel | 600/206 |
| 5,332,095 A | * | 7/1994 | Wu | 206/524.8 |
| 5,339,799 A | * | 8/1994 | Kami et al. | 600/117 |
| 5,363,838 A | * | 11/1994 | George | 600/120 |
| 5,429,142 A | * | 7/1995 | Szabo et al. | 128/849 |
| 5,433,221 A | * | 7/1995 | Adair | 128/849 |
| 5,490,524 A | * | 2/1996 | Williams et al. | 128/849 |
| 5,757,117 A | * | 5/1998 | Hirasawa et al. | 313/479 |
| 5,759,644 A | * | 6/1998 | Stanley | 428/14 |
| 5,812,188 A | * | 9/1998 | Adair | 348/77 |

\* cited by examiner

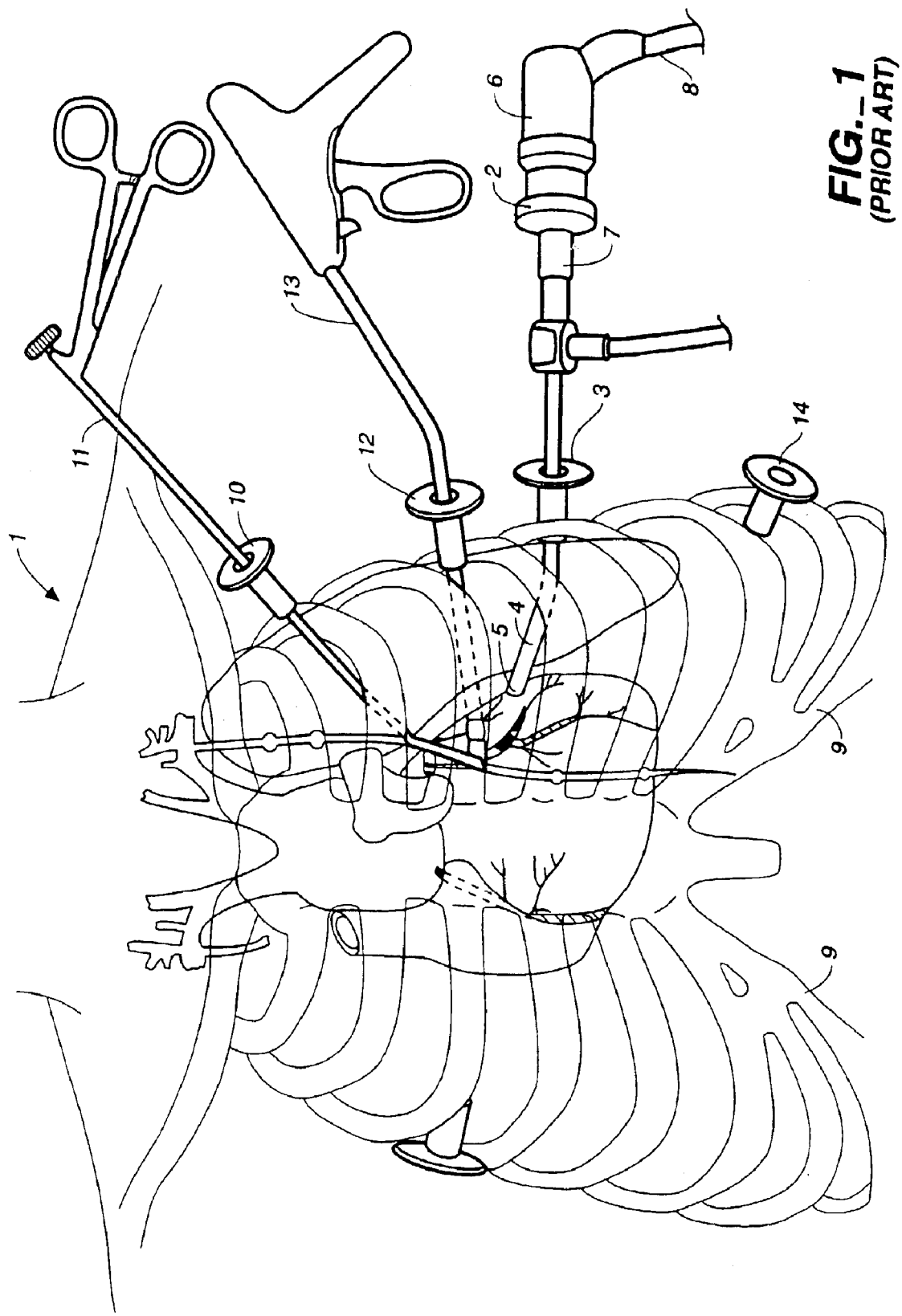
FIG._1
(PRIOR ART)

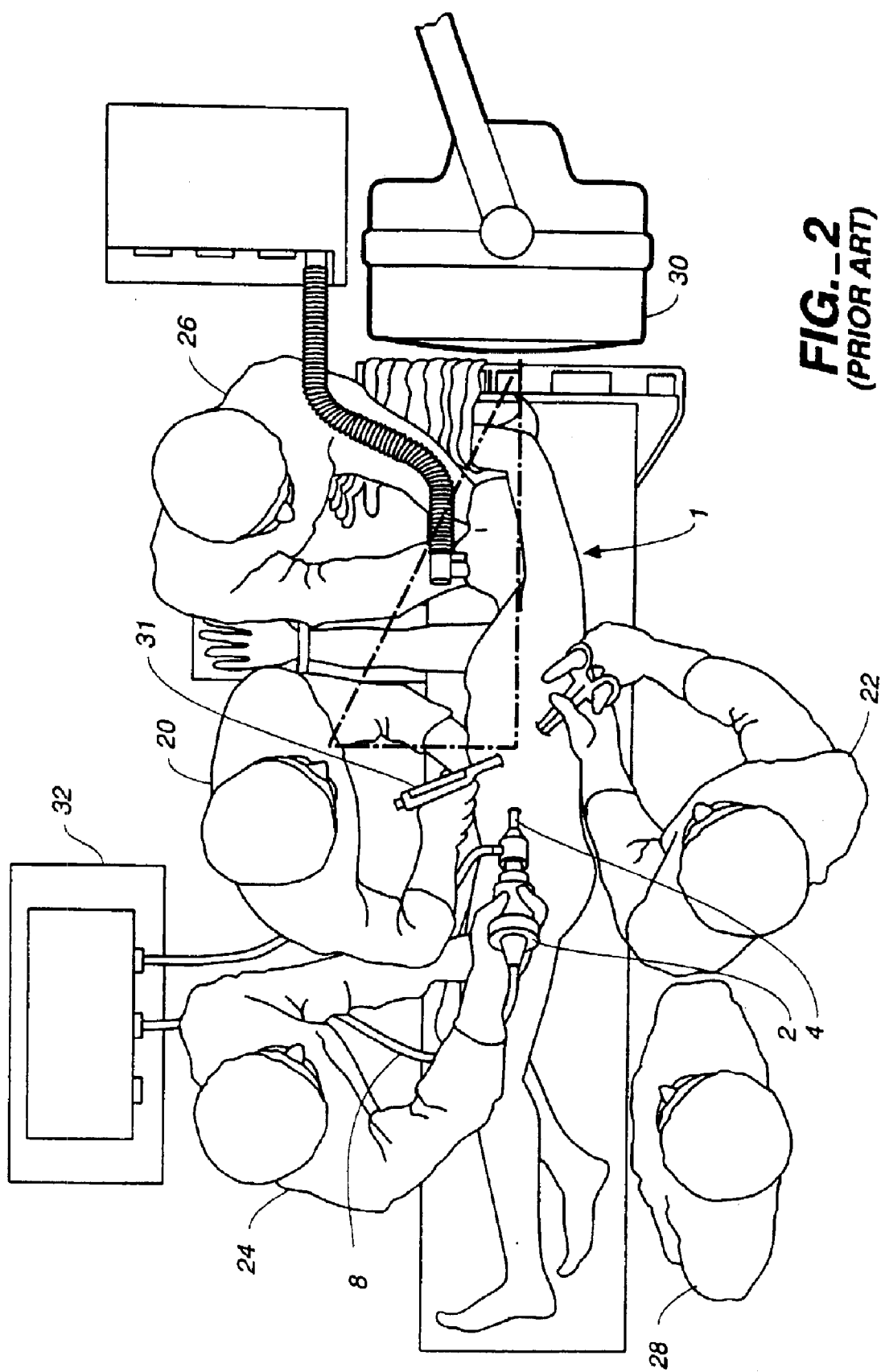
FIG._2
(PRIOR ART)

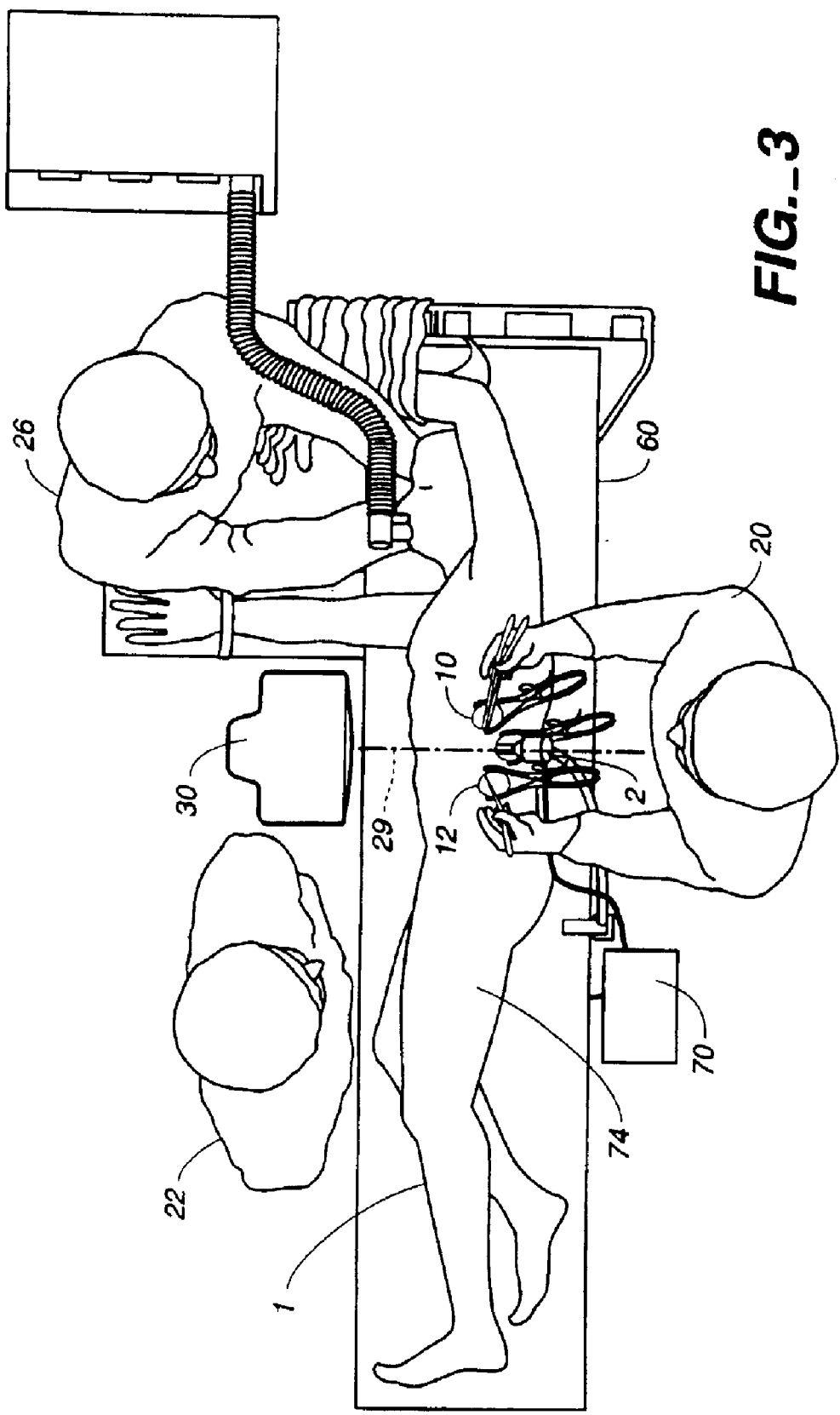
FIG._3

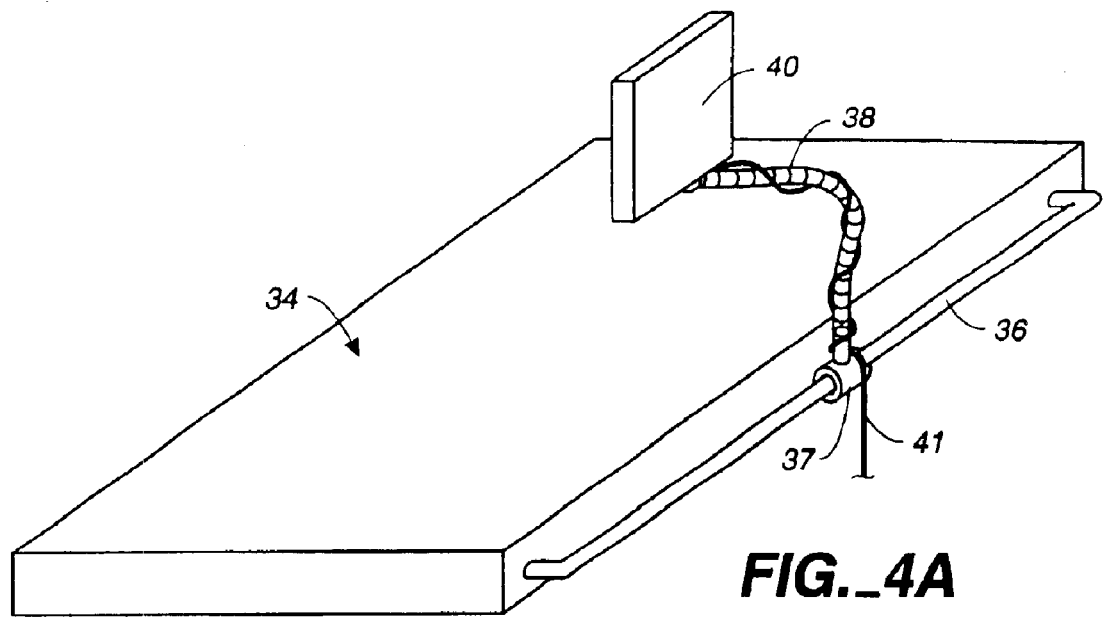
FIG._4A
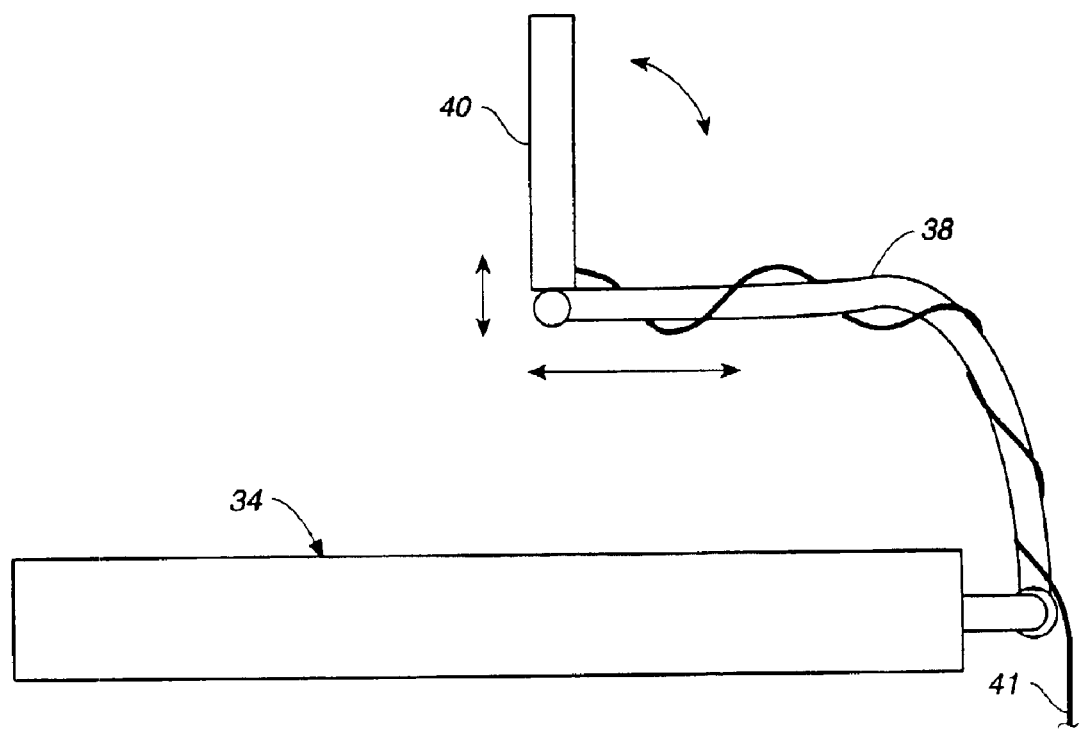
FIG._4B

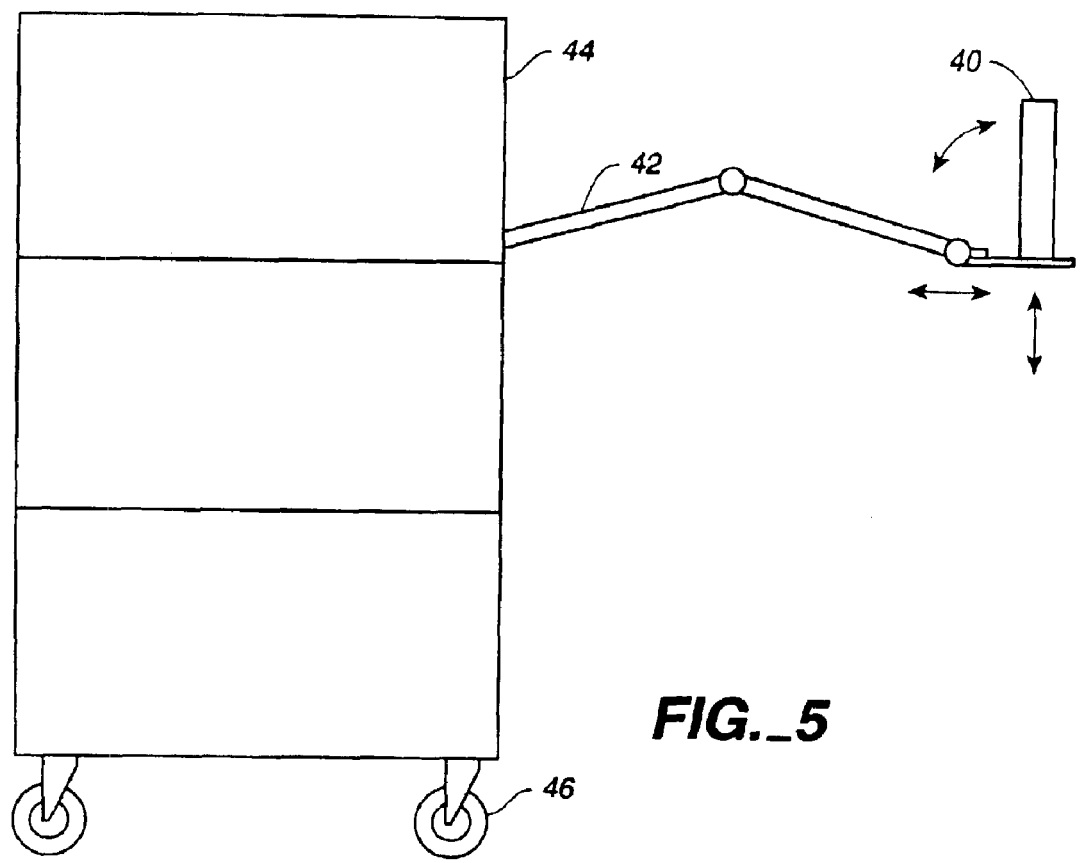
FIG._5

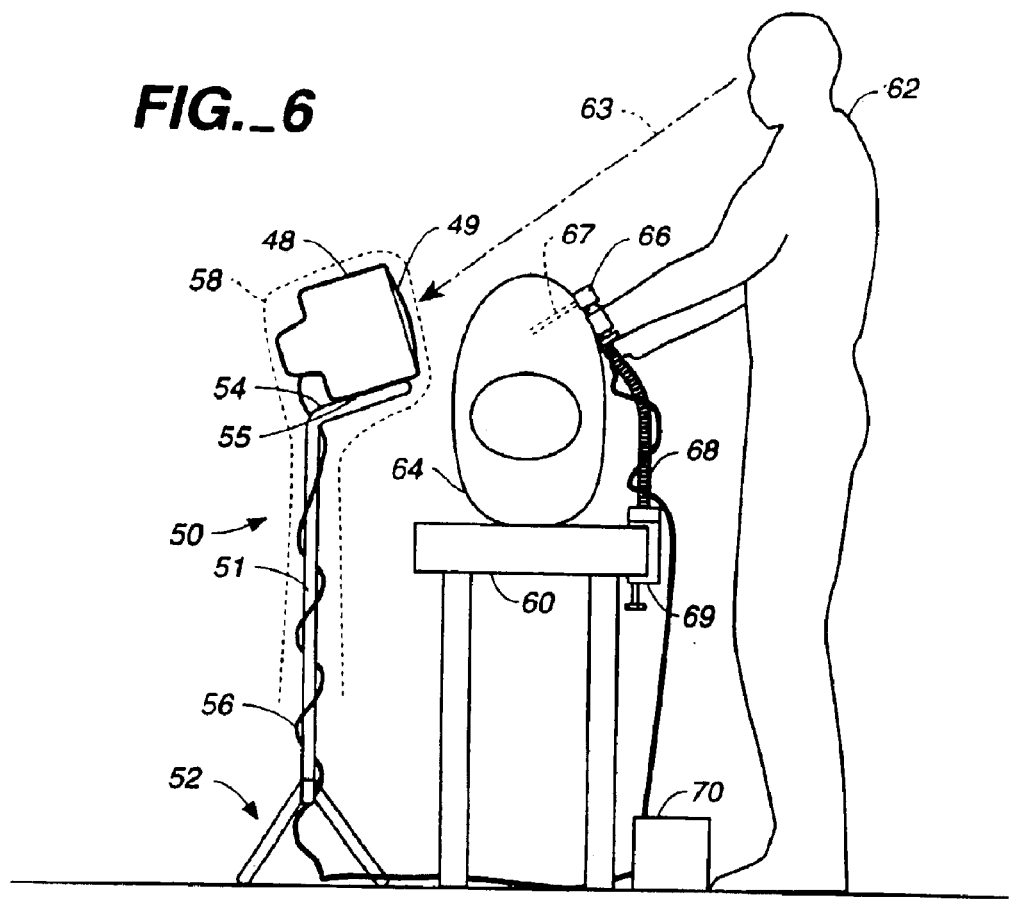
FIG._6
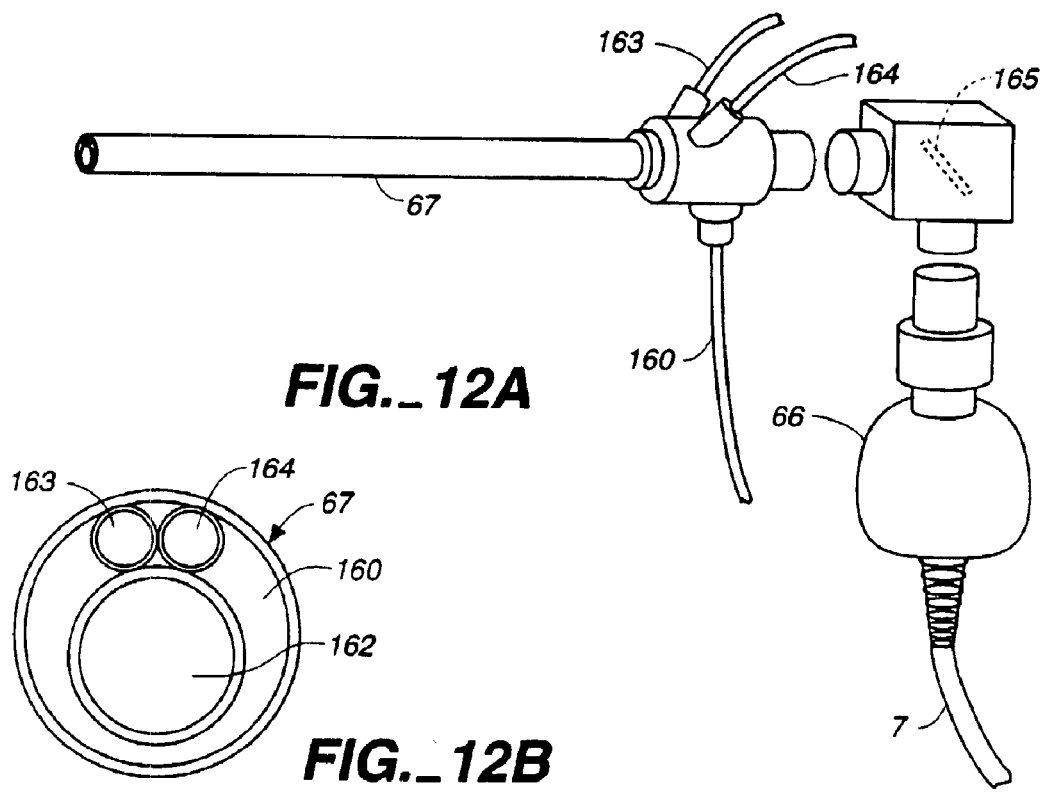
FIG._12A
FIG._12B

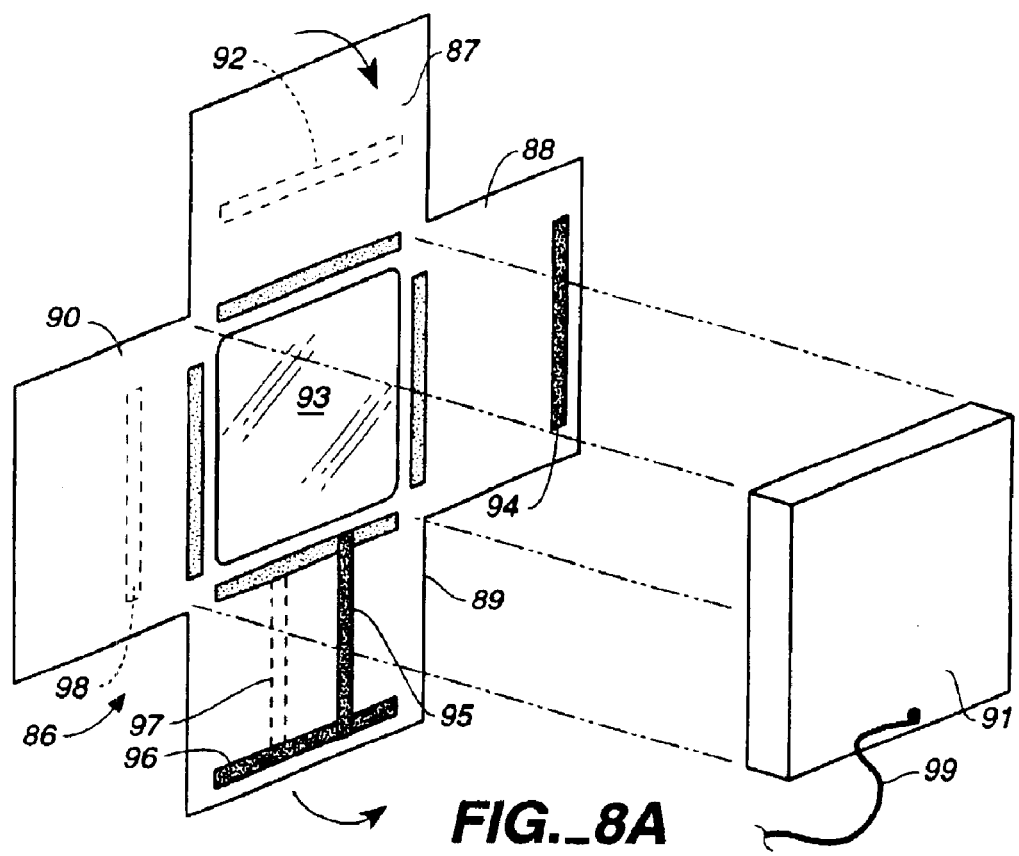
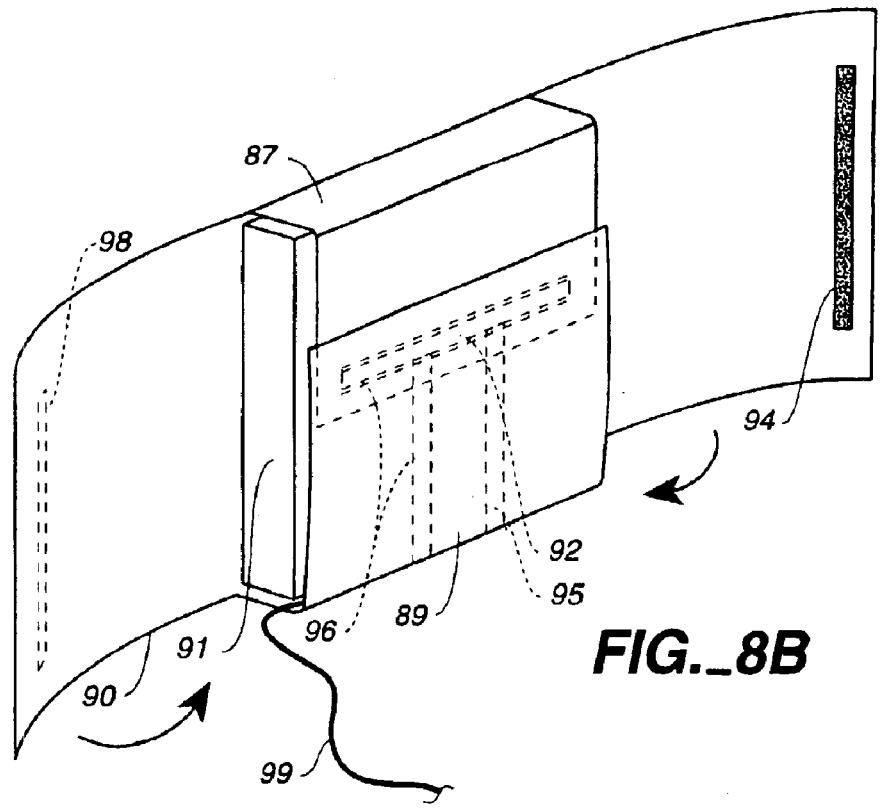

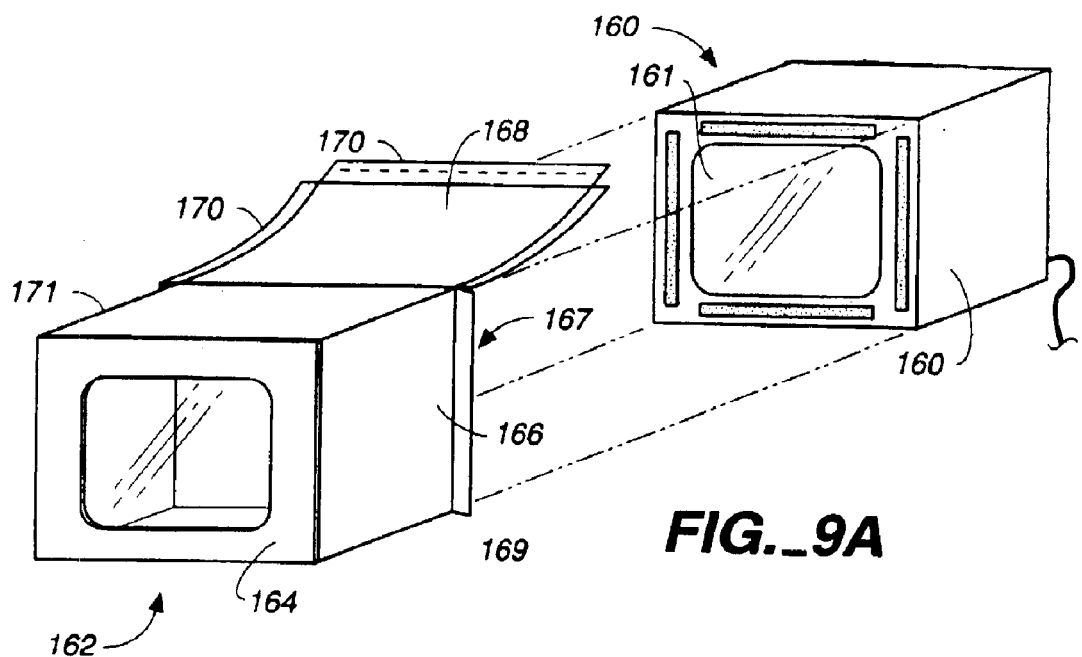
FIG._9A
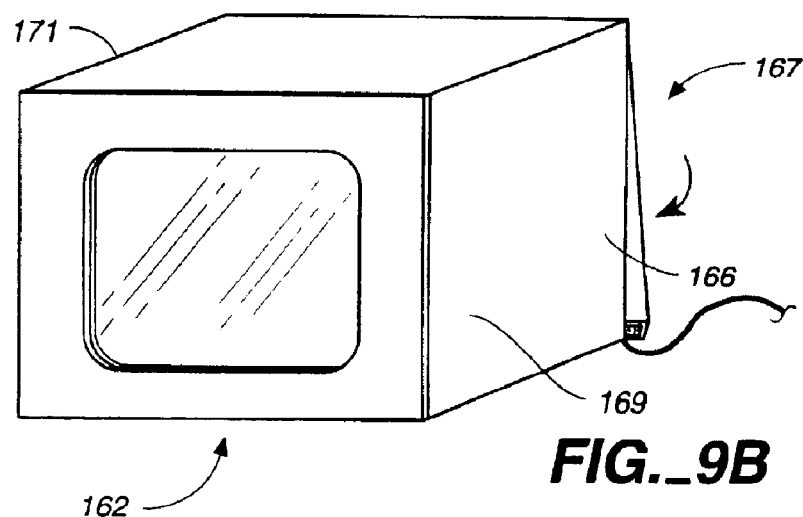
FIG._9B

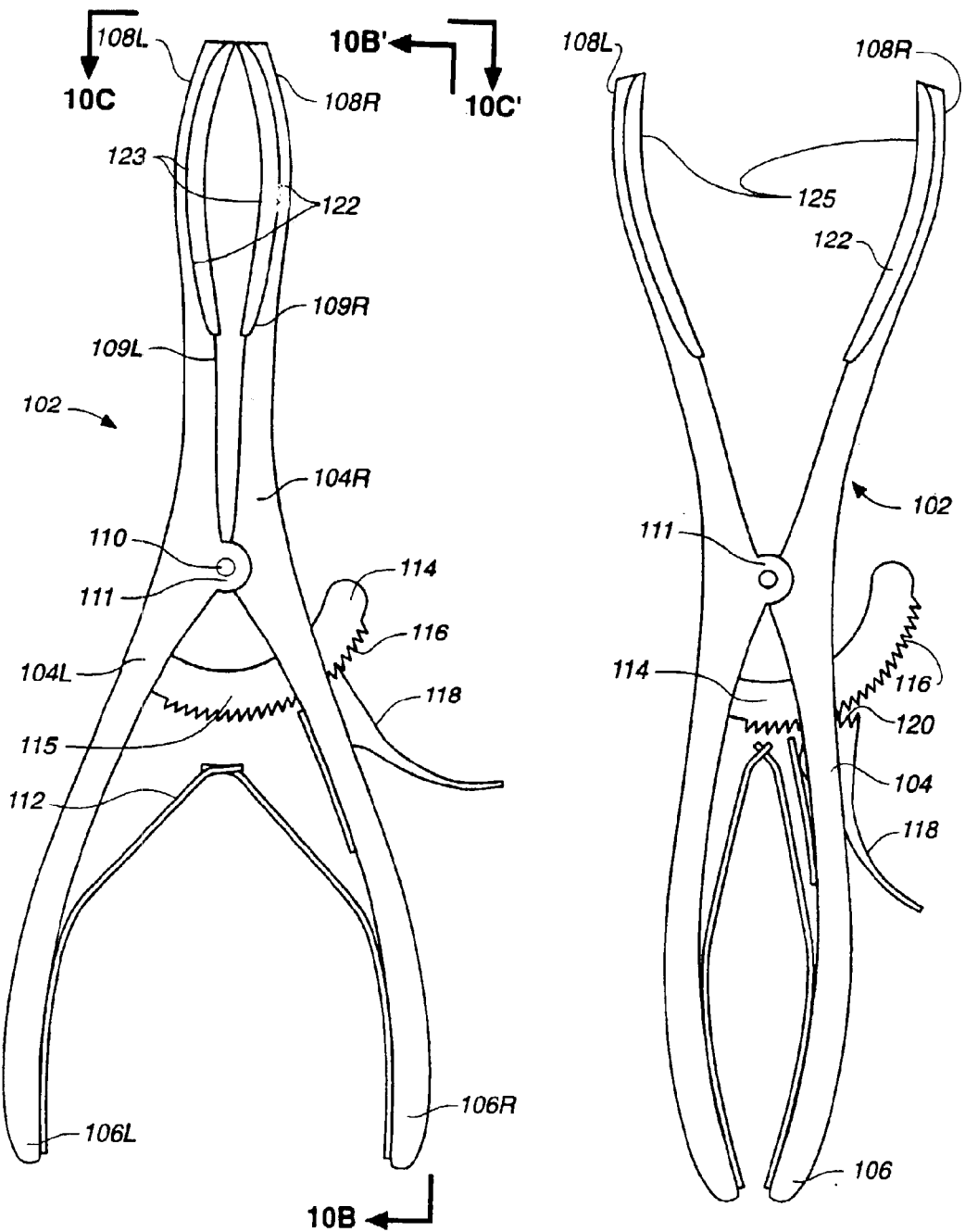
FIG._10A  FIG._10D

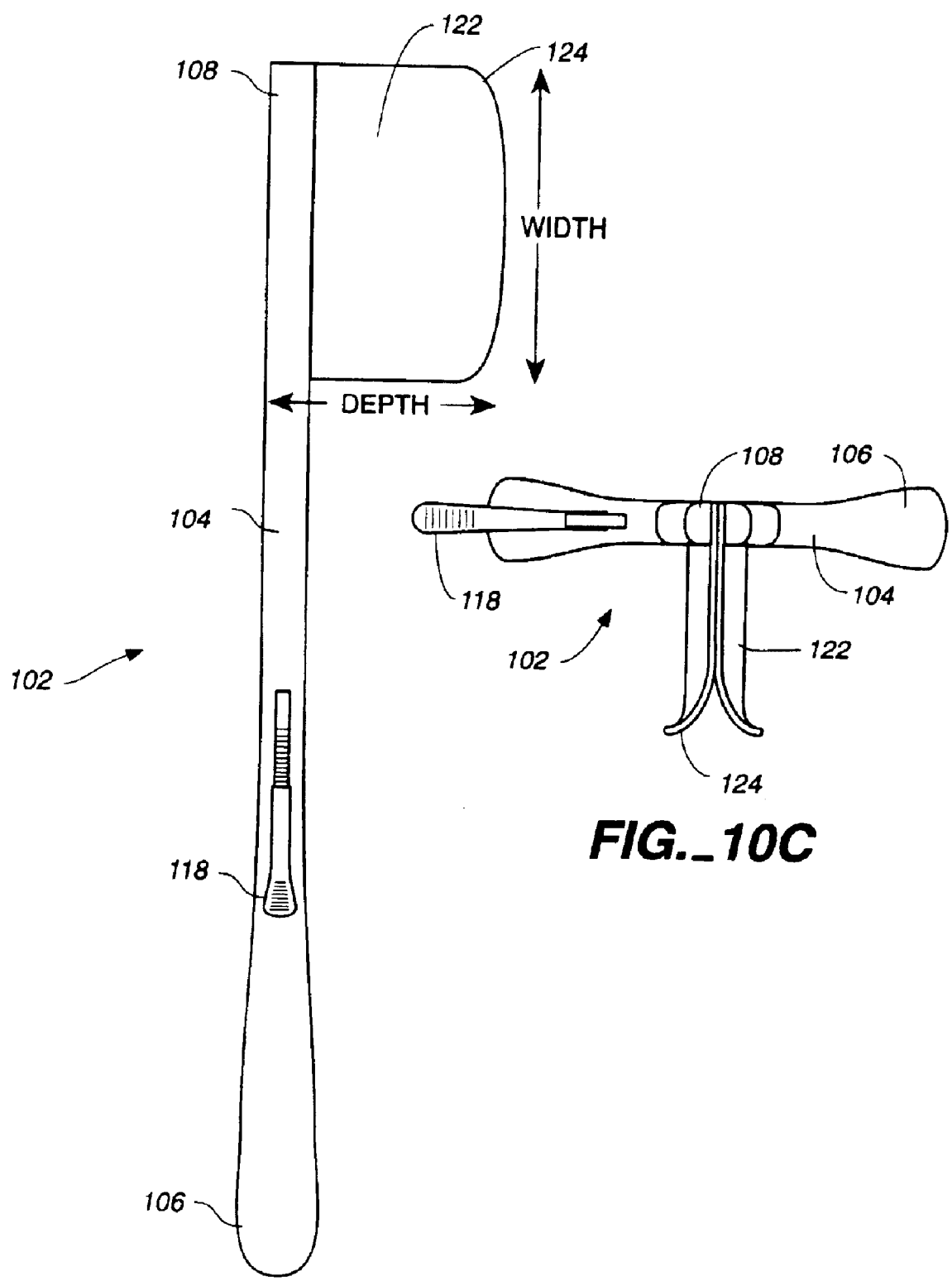
FIG._10B
FIG._10C

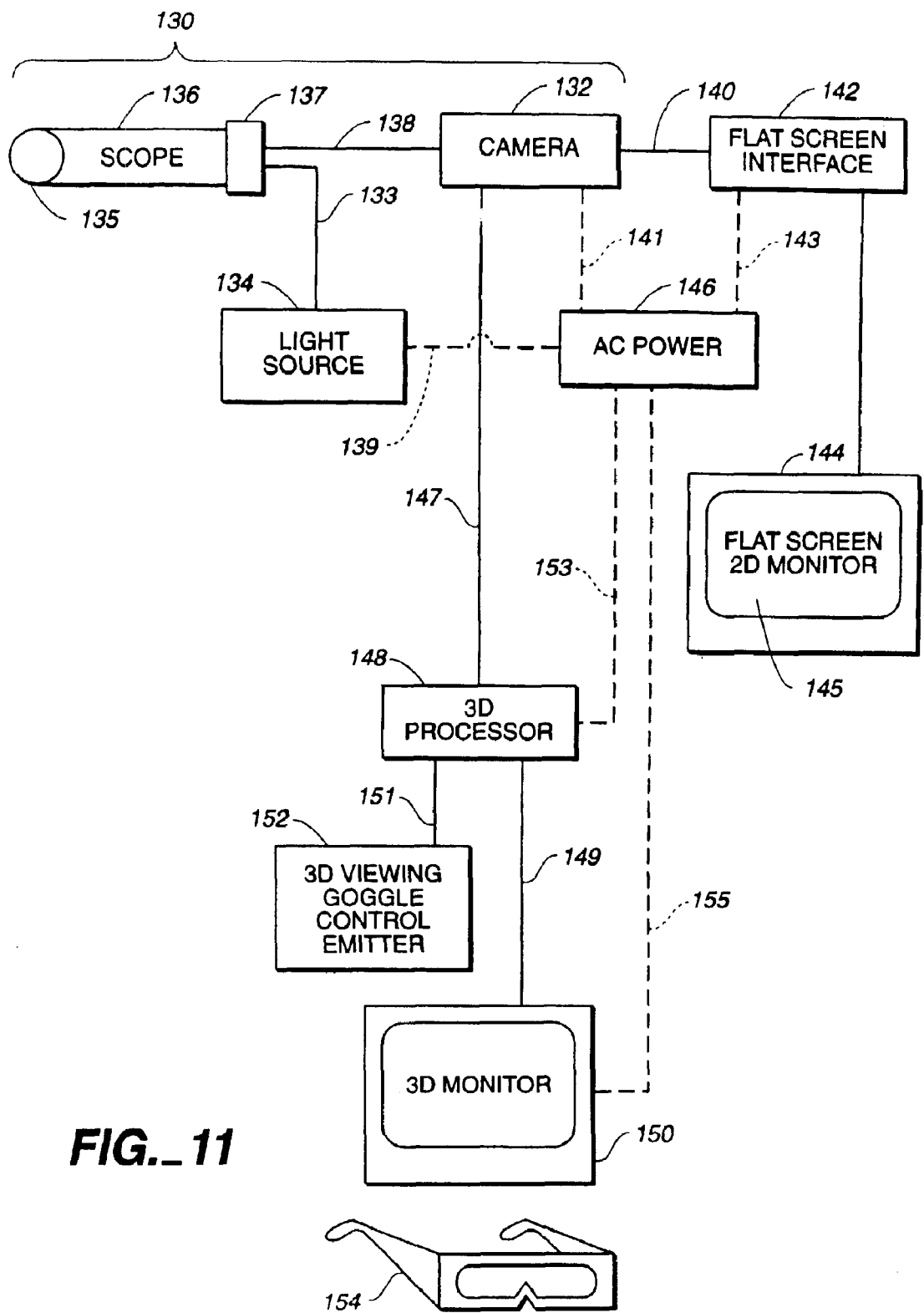
FIG._11

VISUALIZATION DURING CLOSED-CHEST SURGERY

CROSS-REFERENCE TO RELATED APPLICATIONS

This is a continuation of application number 09/672,110 filed Sep. 27, 2000 now abandoned, which is a continuation of application 09/171,206 filed Aug. 10, 1999 now abandoned, which is a National Stage application of international application number PCT/US97/06112 filed Apr. 10, 1997, which claimed the benefit of provisional patent application U.S. 60/014,922 filed Apr. 10, 1996 in the name of inventors Arthur Bertolero, Raymond Bertolero and Jerome Riebman. This application is related to applications PCT/US97/06533, PCT/US97/05910, PCT/US97/06070 and U.S. Utility Ser. No. 08/838,774. Each of the above-identified patent applications is incorporated by reference.

INTRODUCTION

1. Technical Field

This invention relates methods and apparatus for improving a surgeon's ability to perform video-assisted, closed-chest diagnostic and surgical procedures on patients requiring such procedures. It particularly relates to bringing a viewing monitor into the surgical field and positioning the monitor to provide the surgeon with nearly perfect visual alignment so that he or she has the feel of open-chest surgery. This is achieved by using specifically designed surgical drapes for the viewing monitor and apparatus designed to unobtrusively position the viewing monitor within the surgical field.

2. Background

Surgery on the heart is one of the most commonly performed types of surgery that is done in hospitals across the U.S. Cardiac surgery can involve the correction of defects in the valves of the heart, defects to the veins or the arteries of the heart and defects such as aneurysms or thromboses that relate to the circulation of blood from the heart to the body. In the past, most cardiac surgery was performed as open-chest surgery, in which a primary median sternotomy was performed. That procedure involves vertical midline skin incision from just below the super sternal notch to a point one to three centimeters below the tip of the xiphoid. This is followed by scoring the sternum with a cautery, then dividing the sternum down the middle and spreading the sternal edges to expose the area of the heart in the thoracic cavity. This technique causes significant physical trauma to the patient and can require one week of hospital recovery time and up to eight weeks of convalescence. This can be very expensive in terms of hospital costs and disability, to say nothing of pain to the patient.

In recent years, attempts have been made to change such invasive surgery to minimize the trauma to the patient, to allow the patient to recover more rapidly and to minimize the cost involved in the process. New surgical techniques have been developed which are less invasive and traumatic than the standard open-chest surgery and borrow from other types of surgery such as laparoscopic and endoscopic surgeries. This is generally referred to as minimally-invasive surgery. One of the key aspects of the minimally invasive techniques is the use of a trocar as an entry port for the surgical instruments. In general, minimally invasive surgery entails several steps: (1) at least one, and preferably at least two, intercostal incisions are made to provide an entry position for a trocar; (2) a trocar is inserted through the incision to provide an access channel to the region in which the surgery is to take place, e.g., the thoracic cavity; (3) a videoscope is provided through another access port to image the internal region (e.g., the heart) to be operated on; (4) an instrument is inserted through the trocar channel, and (5) the surgeon performs the indicated surgery using the instruments inserted through the access channel while viewing the surgery on a viewing monitor which displays the images transmitted from the videoscope. Prior to steps (1)–(5), the patient is prepared for surgery by placing him or her on a cardiopulmonary bypass (CPB) systems and the appropriate anesthesia, then maintaining the CPB and anesthesia throughout the operation. For discussions of this technique, see U.S. Pat. No. 5,452,733 to Sterman et al. issued Sep. 26, 1995 and an article by Landreneau, et al. entitled "Video-Assisted Thoracic Surgery: Basic Technique Concepts and Intercostal Approach Strategies" Am. Thoraci. Surg. 1992; 54:800–807.

While this procedure has the advantage of being less invasive and traumatic than performing a media sternotomy, several recurring difficulties remain in the process. The present videoscopes are designed such that the surgeon is required to remain away from the patient about 12 to 18 inches because of the linear design of the videoscope. In addition, the visualization of the image of the region in which the examiner is working is offset. This is because the monitoring screen on which the ongoing internal procedure is shown is not in the surgical field. This makes it difficult and uncomfortable for the surgeon to perform the work as he is viewing the screen either a significant distance away from the surgical field or at an angle which is different than he is used to viewing the surgery were it open chest surgery. In addition, having only a two-dimensional viewing monitor makes the surgery process, particularly suturing, difficult to accomplish. By using the apparatus and methods of this invention in the minimally invasive surgery, the surgeon's ease of practice is improved so that the likelihood of success is increased for the patient.

OBJECTS OF THE INVENTION

An object of this invention is to provide an improved method for performing closed-chest, video-assisted diagnostic or surgical treatment of a patient.

Another object of this invention is to provide a video view scope of an improved design to allow a surgeon to stand closer to the patient to whom the surgeon is providing treatment.

Another object of this invention is to provide a surgical drape suitable for enclosing a viewing monitor and positioning the draped monitor in a surgical field of an operating room.

Still another object of this invention is to provide apparatus to position a sterile, draped viewing monitor within the surgical field of an operating room.

Still another object of this invention is to provide improved endoscopic visualization apparatus.

Still other objects of this invention may be apparent to one of ordinary skill upon reading the following specifications and claims.

SUMMARY OF THE INVENTION

One aspect of this invention is an improved method for a closed-chest, video-assisted diagnostic or surgical treatment of a patient. The known method comprises positioning a viewing scope having an elongated nosepiece suitable for gathering and transmitting images to a small video camera so that the nosepiece is inserted through a first percutaneous intercostal opening in the patient to view an internal cavity of the patient requiring diagnostic or surgical treatment and transmitting the image so gathered through the video camera to a viewing monitor, providing at least a second percutaneous opening suitable for inserting a surgical or diagnostic instrument therethrough, inserting a first diagnostic or surgical instrument through said second opening to perform an internal diagnostic or surgical procedure in the patient's cavity while viewing the image of said procedure on the monitor. The improvement comprises (a) draping said monitor with a transparent, sterile surgical drape and (b) positioning said draped monitor within the surgical field so that the surgeon can perform the internal surgical or diagnostic procedure and view it on said monitor so that the surgeon's visual access to the monitor correlates as closely as possible to the visual access of the input end of the viewing scope. Preferably the viewing monitor is a flat panel monitor that is on a movable cart having a sterilizable adjustable arm that allows the monitor to be positioned within the surgical field and adjusted to enhance the surgeon's visual alignment.

Another aspect of this invention is a flexible sterile drape for covering a video monitor within the surgical field of an internal operation to be performed on a patient, which drape comprises a transparent field within perimeter of the drape and positioned to cover the viewing panel of said monitor and fastening means around the perimeter of the drape for completely covering a video-monitor to ensure the monitor's sterility and suitability for retaining within a surgical field during a diagnostic surgical treatment of a patient.

Another aspect of this invention is a video monitor device for use within the surgical field of an operation being performed on a patient, said device comprising a video monitor enclosed by a transparent, flexible sterile drape so that the screen transmits a clear image through said drape and the enclosed monitor is sterile.

Another aspect of this invention is an apparatus for assisting a surgeon in performing closed-chest, video-assisted surgical or diagnostic treatment of a patient. The apparatus comprises a movable cabinet, an adjustable arm having its proximal end attached to the cabinet and having the distal end of said arm extendable outwardly from the cabinet, and a platform securely attached to the distal end of the adjustable arm. The platform is designed to securely receive and attach a viewing monitor and the adjustable arm is extendable outwardly to position the viewing monitor within the surgical field of an operating room without having the cabinet extend into to surgical field.

Still another aspect of this invention is an operating table for assisting a surgeon in performing a closed-chest, video-assisted surgical or diagnostic treatment of a patient. The table comprises a flat, horizontal support means supported by vertical legs attached to the support means, having a field extending above said horizontal support means, an adjustable arm having its proximal end attached to the horizontal support means and having the distal end of said arm extendable into said field above said horizontal support means, and a platform securely attached to the distal end of the extendable arm. The platform is designed to securely receive and attache a viewing monitor to it so that the viewing monitor is positioned within the field.

Still another aspect of this invention is an endoscopic visualization apparatus. The apparatus comprises a view scope having a light source, camera, and lens means, wherein the view scope has the lens means positioned in a nosepiece designed to be inserted percutaneously into a patient's internal cavity to gather and transmit an image from the distal end of the lens means to said camera;

signal transmission cord from said camera to a signal processing unit;

power transmission cord for the light source, camera and signal processing unit;

the signal processing unit capable of interpreting the signal from the camera and of transmitting a signal to a viewing monitor through a signal transmission cord, and a view monitor capable of exhibiting the image gathered from the patient's cavity on a screen portion of the viewing monitor, wherein said camera is positioned at about a 90 degree angle to said nosepiece to minimize the distance said view scope extends out of said patient.

Still another aspect of this invention is a view scope having a light source, camera, and lens means, said view scope having the lens means positioned in a nosepiece designed to be inserted percutaneously into a patient's internal cavity to gather and transmit an image from the distal end of the lens means to said camera, wherein said camera is positioned at about a 90° angle to said nosepiece to minimize the distance said view scope extends out of said patient.

Other aspects and preferred embodiments will be apparent to one of ordinary skill upon reading the following specification and claims.

BRIEF DESCRIPTION OF THE DRAWINGS

FIG. 1 shows a cutaway view of closed-chest surgery known in the art.

FIG. 2 shows a top view of a surgical team performing a method known in the art.

FIG. 3 shows a top view of a surgical team using the improved method of this invention.

FIG. 4A is a perspective view of the upper portion of an operating table having an adjustable arm for use in this invention.

FIG. 4B is an end view of the table of 4A having a viewing monitor attached to the adjustable arm and showing the direction of adjustability.

FIG. 5 shows a movable cart with an adjustable arm with a viewing monitor thereon.

FIG. 6 shows a side view of a method and apparatus of this invention.

FIG. 8A shows an exploded perspective view of how a cruciform configuration of a sterile drape of this invention encloses a flat panel viewing monitor.

FIG. 8B shows a perspective view of the sterile drape of this invention partially enclosing the flat panel viewing monitor.

FIG. 9A shows an exploded perspective view of the sterile drape in the form of a sleeve having a folding flap about to enclose a viewing monitor.

FIG. 9B shows a perspective view of the sleeve drape of FIG. 9A partially enclosing a viewing monitor.

FIG. 10A shows a top view of a surgical retractor useful in the method of this invention.

FIG. 10B shows a side view of the retractor of FIG. 10A along lines 10B–10B'.

FIG. 10C shows an end view of the retractor of FIG. 10A along lines 10C–10C'.

FIG. 10D shows a top view of the retractor of FIG. 10A in the open position.

FIG. 11 shows a schematic diagram of how the portions of the visualization apparatus of this invention fit together.

FIG. 12A shows a perspective view of the view scope of this invention.

FIG. 12B shows an end view of the view scope of FIG. 12A.

DETAILED DESCRIPTION AND PRESENTLY PREFERRED EMBODIMENTS

Figure 7:
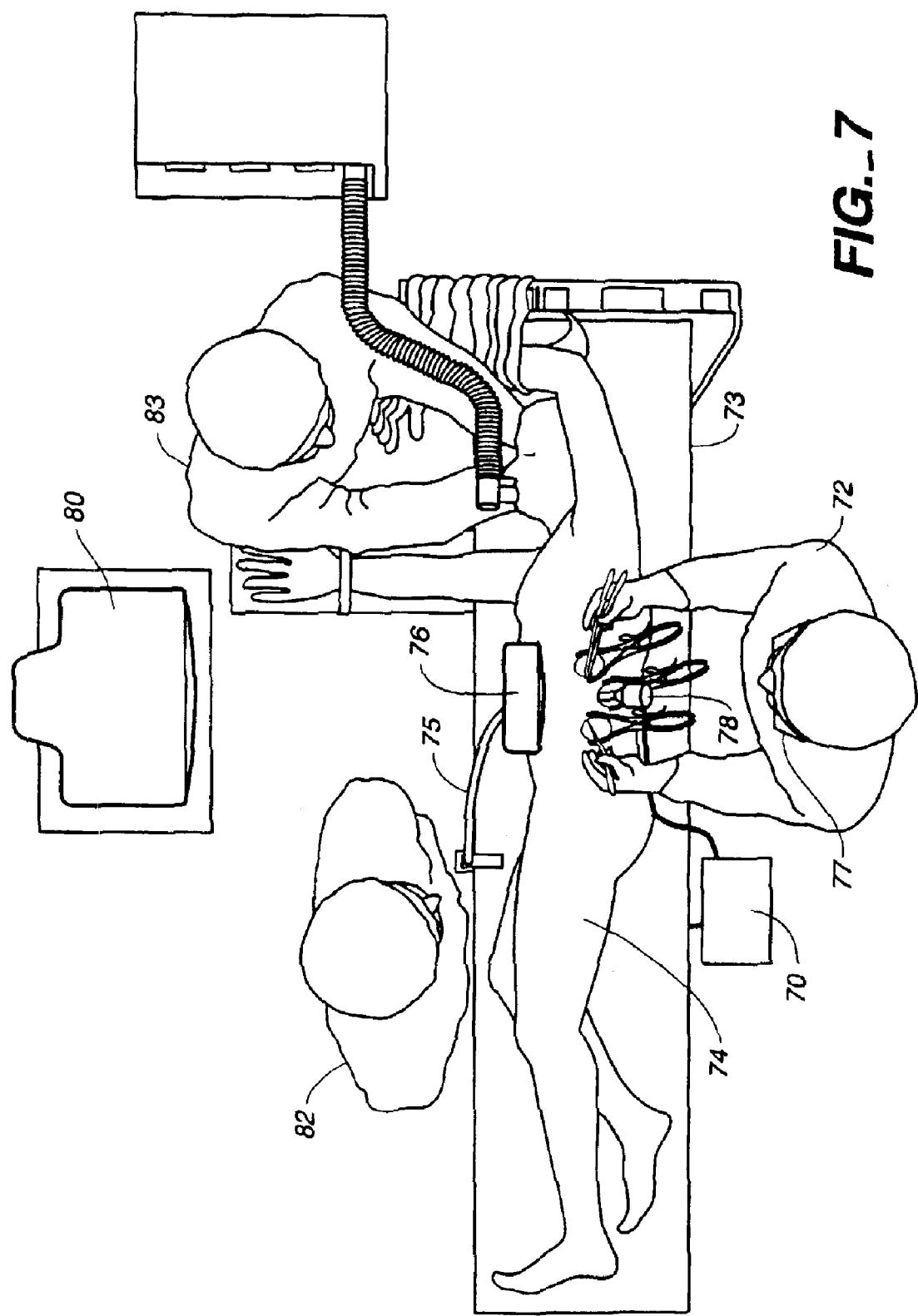
FIG. 7 shows a top perspective view of how to perform certain preferred aspects of the method of this invention.

One aspect of this invention can be considered an improvement of a method for video-assisted, closed-chest diagnostic or surgical treatment of a patient, particularly for cardiac surgery. The improvement is to an existing method that requires the use of a viewing scope (e.g. a thoracoscope or an endoscope) to carry out a surgical procedure. A viewing scope comprises a miniature video camera with a lens means, a light source and transmission means, a processing unit for forming an image and a transmission means for transmitting the image to a viewing monitor. The lens means and light transmission means is usually in a nosepiece that is inserted through a percutaneous hole in the appropriate position of the patient and positioned so that the lens gathers the image that ultimately is transmitted to the viewing monitor. Suitable viewing scopes include those made by Olympus, Solos, Starz, Medical Dynamics, Feijinan, Wolf, Stryher, Linvatic, ACMI, Pentax, Dyonics and Concept. These are available, for example through United Endoscopy, 350 S. Milliken Avenue, Suite B, Ontario, Calif. 91761-7845. A particularly useful view scope is available from Vista Medical Technologies, Carlsbad, Calif. For example the Vista model on 9000 (3-chip camera), on 4000 (light source) and OT 2000 (Thoracoscope) combine to make a useful view scope for the known method.

Generally the existing method comprises positioning a viewing scope having an elongated nosepiece so that the nosepiece is inserted through a first percutaneous intercostal opening in the patient to view an internal region of the patient (e.g., the heart) requiring the surgical or diagnostic treatment. The image so gathered is transmitted through the video camera to a viewing monitor (i.e., a video screen) which can be viewed by the surgeon who is performing the surgical treatment. Generally, at least one additional percutaneous opening, and preferably at least two, and as many as up to five, are provided for inserting surgical instruments therethrough. A surgical instrument is inserted through the instrument opening to perform an internal surgical procedure on the patient's heart or associated vasculature while viewing the image of the procedure on the monitor. The improvement of this invention comprises (a) draping the viewing monitor with a transparent, sterile surgical drape and (b) positioning the draped monitor within the surgical field so that the surgeon's visual access to the monitor correlates as closely as possible to the visual access of the input end of the viewing scope. This provides a sense of operational visual reality to the surgeon, that is, the surgeon sees the results of the internal operation in a manner and in a position as if he is performing the surgery in an open-chest operation. This provides the surgeon with the "feel" of operating on an open heart, for example. The improvement generally works best when there are at least two percutaneous openings that are suitable for inserting surgical instruments therethrough and the viewing scope is positioned intermediate the two so the operational visual reality is enhanced by allowing the doctor to manipulate the instruments with his right and left hands while viewing the monitor directly in front of him and close enough so that he has nearly perfect visual alignment with the screen. When the monitor is a flat panel monitor the feel to the surgeon is particularly enhanced if the flat panel is placed in a position in close proximity to the patient so the doctor can view the operation at a distance which approximates the distance he would be seeing the operation were it open-chest surgery. The surgical field is that region of an operating room within which everything must be essentially sterile to minimize the chance of infection in a patient. This will include the operating table on which a patient is positioned and any equipment located or used within the boundaries defined by vertical extensions of the perimeter of the table.

The viewing monitor may be placed into the surgical field by one of several means. A sterilizable stand having an adjustable arm can be used to affix the draped monitor to or the monitor can be affixed to the adjustable stand and the sterilizable drape placed over the monitor after it is on the stand. The stand is movable, has an adjustable arm means and a holding means on the arm means to hold the viewing monitor. The arm means is then adjusted to position the monitor within the surgical field. For example, the stand would have a stable base means with a substantially vertical shaft that is adjustable and that has an arm off the vertical shaft with a means for attaching the monitor. Both the length of the arm and the length of the shaft are adjustable for placement in accordance with the needs of the surgeon. Alternatively, the monitor can be carried by a cart having an adjustable arm attached to it. Generally, the cart will be easily mobilized and will have lockable wheels which can be used to move the cart around the operating room and lock it in place once positioned. The adjustable arm upon which the monitor sits may be adjustable and lockable into a position, but is long enough to reach into the surgical field to provide the surgeon with nearly perfect visual alignment. Alternatively, a flexible and adjustable arm can be attached to the operating table where the arm is sterilizable and has a means to fasten the monitor to and hold it within the surgical field. Each of these alternatives will be discussed in greater detail hereinafter.

Another aspect of this invention is a flexible sterile drape for covering a viewing monitor within the surgical field of a surgical operation carried out on a patient. The drape comprises a transparent section within the perimeter of the drape that is positioned to cover the viewing panel of a monitor. The drape has fastening means around the perimeter of the drape for completely covering a video monitor to ensure the monitor's sterility and suitability for retaining within the surgical field during the surgical operation. Preferably, for ease of manufacture, the sterile drape of the invention is transparent and is prepackaged in a sterile package. This allows for easy preparation prior to each operation so that the viewing monitor can be draped to ensure sterility simply by opening the sterile package and wrapping the drape around the monitor and positioning the monitor where desired within the surgical field to ensure operational visual reality to the surgeon. Generally, the drape will be made of a transparent plastic material which will allow the transmission of the images on the screen of the viewing monitor through the material so the doctor's vision is essentially unimpaired. This plastic material may be of a polyvinyl chloride (PVC), polyethylene, polypropylene, polycarbonate or some other appropriate polymers. The flexibility of the material is such that it can be bent to surround the viewing monitor and can have the various degrees of stiffness from being much like a piece of cloth with substantial "drapability" to being fairly stiff and foldable. Generally, the sterile drape will have perimeter fastening means so that the drape can have interlocking portions to ensure that it fits around the monitor and is permanently fastened during the surgical procedure. A material that is particularly useful in this regard is Velcro hook and loop fastener. Velcro hook and loop fastener strips are placed on the perimeter so that they can either interact with a corresponding strip on the monitor or will interact with a corresponding strip on the opposing side of the drape so that the strips can interlock and hold the drape in place on the monitor. Alternatively, the perimeter fastening means could be a series of adhesive strips that are sufficient to either adhere to the monitor itself or to adhere to the opposing side of the drape. Still another alternative would be to use interlocking snaps on the perimeter of the drape to allow the viewing monitor to be fully covered and sterile for use within the surgical field. In some cases, the flexible, sterile drape is designed to have an adhesive that is located on the side of the drape that is to lay against the screen of the viewing monitor. The adhesive is layered on the appropriate side of the drape in a pattern that fits around the perimeter of the screen to ensure a tight fit against the screen. Alternatively, the drape may be designed as a sleeve or box into which the viewing monitor slips and is then enclosed with a foldable flap to cover the monitor. In such a case it is useful to provide a flat, stiff frame around the monitor screen to provide a snug fit of the drape over the monitor to avoid any distortion in the transparent drape.

Thus, another aspect of the invention is a viewing monitor device for use within a surgical field of an operation being performed on a patient. The device comprises a viewing monitor enclosed by a transparent, flexible sterile drape so that the screen of the monitor transmits a clear image through the drape. The drape encloses the monitor to ensure that the device is sterile for the purposes of the operation.

Turning now to FIG. 1, one sees a cutaway view of an approach to closed chest surgery that is set out in U.S. Pat. No. 5,452,733. In this example of a method that is known in the art one sees the patient generally designated as 1 having a series of percutaneous openings 3, 10, 12, and 14, each of which are shown as having a trocar in the opening. Through percutaneous opening 3 a viewing scope generally indicated as 2 is shown. The nosepiece 4 of the view scope is shown as being inserted through trocar 3 to be positioned to view the internal region being operated upon. The nosepiece has a distal end 5 at which point the images are gathered and passed through the nosepiece and a proximal end 7 which is attached to the video camera 6. The view scopes known in the art are generally of the design shown. This suffers from the disadvantage of extending out of the patient about 12–24 inches, depending on the brand. This forces the surgeon away from the patient and makes the operation more difficult for the surgeon. Often another surgeon or assistant must manage the scope to get it out of the way. Transmitting cable 8 then transmits the image to the viewing monitor, not shown. Each of the percutaneous openings are located in the intercostal space between ribs 9. Through opening 10 and 12 are inserted instruments 11 and 13 respectively that can be used by the doctor to assist in the performance of the surgery.

In general, when performing the surgery shown in cutaway, detail in FIG. 1, the surgical team is located as shown in top view FIG. 2. Generally, there is a first surgeon 20 who performs certain of the surgical operations, a second surgeon 22 who also may perform certain of the operations and a camera operator 24, who is surgically trained to operate the viewing scope shown as 2 in FIGS. 1 and 2. Generally, an anesthesiologist 26 will be available to ensure that the anesthesia is properly applied to the patient and there will be at least one additional assistant 28 to aid in the operation. The viewing monitor 30 is situated outside the surgical field as it is not sterile. The view from the surgeon 20 is one of triangulation as shown by the triangle 31 wherein surgeon 20 uses the screen from one angle. Surgeon 20 uses the screen from another angle. A cardiopulmonary bypass machine operates to ensure the patient 1 has sufficient blood flowing through his system to maintain his bodily functions.

FIG. 3 is a top view of the surgeon operating using the improvement of the present invention. Here, the patient 1 is being operated on by surgeon 20 using instruments that are inserted through percutaneous openings 10 and 12. The viewing scope 2 is situated such that the distal end of the nosepiece provides a view of the region being operated upon. The image is transmitted then to the viewing monitor 30 which is shown as being within the surgical field and is appropriately draped in accordance with the invention. The dotted line 29 shows the surgeon's visual alignment which is nearly perfectly aligned to ensure operational visual reality to the surgeon. Thus, by using the improvement of the invention, the progression of the internal operation is shown on the screen of the viewing monitor in a manner and in a position that gives the surgeon the sensation that he is performing the surgery topically, that is, the operation would have the approximate feel to the surgeon of operating on an open heart. This allows the surgeon to perform the operation more comfortably and increases the likelihood of success in the operation. Also shown in FIG. 3 are surgical retractors, not numbered, that are particularly valuable for providing access to the patient's internal thoracic cavity, for example. The retractors have the advantage of providing the surgeon with a greater degree of range of motion when he or she inserts appropriate surgical instruments through the elongated access opening to perform diagnostic, exploratory or surgical procedures. The unique surgical retractors and their use are discussed elsewhere in this specification.

Turning now to FIG. 4A (another aspect of the invention) which shows a perspective of the upper portion an operating table 34 upon which a patient can be positioned for performing cardiac surgery. The table will have a support means shown as bar 36 attached to the edge of the table upon which an adjustable arm 38 is connected with clamp 37. The end of the adjustable arm 38 that is proximal to the table is attached to bar 36 through clamp 37 and the end that is distal to the adjustable arm 38 holds the viewing monitor 40. The adjustable arm can be moved along bar 36 by loosening clamp 37. This can be attached by having a flat plate at the end of the adjustable arm to which the viewing monitor can be firmly connected to by a suitable manner, e.g., screws, bolts, belts and the like. The monitor can be swiveled on the plate so that it can be positioned at any position from a substantially perpendicular position shown in 4B to a closer to horizontal position. In addition, the adjustable arm can be moved up and down as well as back and forth relative to the longitudinal axis of the table. These are shown by the three sets of arrows in FIG. 4B. If the surgeon stands to the left of the table shown in FIGS. 4A and 4B, the viewing monitor 40 can be adjusted as desired. The viewing monitor 40 will be draped with the surgical drape as will the adjustable arm 38 and the electrical cord 41 and other necessary cords to transmit the image to the panel from the view scope inside the patient. By ensuring the sterility of the viewing monitor and the adjustable arm and cords by draping with the sterile surgical drape, the surgeon is able to maintain nearly perfect visual alignment during the operation so that the, feel of the operation is very similar to operating under open chest conditions.

A useful flat panel viewing monitor is available from CTX Opto, Inc., 1257 Tasman Dr., Sunnyvale, Calif. The monitor having a 12.1 inch viewable diagonal screen size with a resolution of 800 pixels (horizontal) and 600 lines (vertical) is particularly useful. The synchronization frequencies are: Horizontal scan—24 KHz to 50 KHz; Vertical refresh—56 Hz to 75 Hz; and pixel frequency 50 MHz. Input signal specifications are: Video; Analog RGBO7Vp-p; Sync: Separate Sync, TTL level and composite sync; TTL level; and Connector: Standard 15 pin RGB. A useful interface for such a flat screen display is part #95.53101.001 and video signal enhancement is available as part #QD 7500 from QD Technology, Inc., Los Gatos, Calif. or an equivalent from Faroudja Labs, Sunnyvale, Calif.

Turning now to FIG. 5 still another alternative is shown to position the viewing monitor within the surgical field to assist the surgeon in maintaining visual alignment in performing the operation. Here, cart 44 is shown with an adjustable arm 42 attached thereto for holding monitor 40. The cart is mobile and can be moved by pushing about the operating room on the wheels 46, that have locking means, not shown. A particularly useful cart is available from Promedica, Inc., 550 Airport Blvd., Tampa, Fla. as model number 120. An example of an adjustable arm that can be modified for this invention is model #69055 from Mediflex, 250 Gibbs Rd., Island, N.Y. The cart may contain the electronics necessary for ensuring the view transmitted from the view scope inside the patient to the viewing monitor. By draping the viewing monitor as well as the adjustable arm and the electrical cords leading to the viewing monitor, the sterility of the monitor and the viewing arm are ensured so that the viewing monitor can be placed within the surgical field to ensure the visual alignment for the surgeon.

Turning now to FIG. 6, one sees another alternative for positioning the viewing monitor within the surgical field. Here, the viewing monitor is shown as a regular television screen instead of a flat panel as shown in the previous figures. The viewing monitor is shown to sit on an adjustable stand 50. The stand comprises a base means shown as three legs for stabilization, a vertical arm 51 and a horizonal arm 54 extending perpendicular to the vertical arm. The horizontal arm is designed to have a base 55 which is suitable for placing the viewing monitor upon and fastening thereto. The viewing monitor 48 is shown as being covered by a surgical drape 58 (shown by the dotted line), which is shown to cover not only the monitor but also the monitor base 55, horizontal arm 54 and vertical arm 51 around which is wound the power cord 56 which is attached to a power source and transmission box 70. The viewing monitor 48 is shown to be within the surgical field and line of vision of the surgeon. Table 60 is shown to have patient 64 resting thereon with surgeon 62 positioned to perform an operation on the patient. The surgeon's line of sight 63 is such that he has a direct view at the viewing monitor screen 49 to provide the best visual alignment for the surgeon. The view scope 66 is positioned within the patient and is shown to have nosepiece 67 inserted within the patient and positioned appropriately. The view scope is held by flex arm 68 attached to table 60 by clamp 69. Once the patient is prepared for the operation, the surgeon 62 may then insert instruments through opening 65A and 65B to perform the diagnosis or surgery as necessary. While the view of the surgeon in FIG. 6 improves his visual alignment over the situation known in the art, it is preferred that the viewing monitor be a flat panel that can rest within the surgical field much closer to the patient. This can be best done by using the device of FIGS. 4A and 4B or the device shown in FIG. 5 so that the flat panel can be positioned nearly directly above the patient so the surgeon's view is perfectly aligned to give the surgeon the feel of performing an open-chest operation.

Another important aspect of this invention is the use of a specially designed surgical retractor to provide the percutaneous openings that are suitable for inserting a surgical or diagnostic instrument therethrough. Presently, the method of choice for providing a channel through which instruments can be inserted is to make an incision in the patient generally intercostally and inserting a trocar into the incision by screwing the trocar into the tissue. The trocar has an internal channel through which the instruments are inserted. This can be seen in FIG. 1 with trocars 10, 12, 14 and 3. However, the channels of the trocars are cylindrical in shape, are relatively narrow and are difficult to manipulate instruments through unless you have a specifically designed instrument such as that shown in the figure and further described in U.S. Pat. No. 5,452,733. We have found that by using a surgical retractor that is described in co-pending patent application attorney docket number ESTC-001/02U.S. (U.S. Ser. No. 09/171,207 now U.S. Pat. No. 6,309,349) filed even day herewith, the surgeon's sensitivity to the use of the instrument is substantially enhanced which, in combination with the improved visualization alignment, gives the surgeon an even greater sense of operating similar to an open chest environment. The details of the ESTC-001/02US application are incorporated herein by reference in their entirety.

The surgical retractor useful in this invention can be used for direct access to an internal organ for surgical purposes with direct viewing of the work that's going on but it is preferably used in conjunction with video assisted cardiac surgery. In the process of this invention, the surgical retractor is used in combination with the view scope (i.e. a video endoscope) that is positioned through a similar surgical retractor, through a trocar or a percutaneous access opening which allows the scope to be positioned such that the internal work on the section to be operated on is transmitted to a screen and the surgeon then performs the operation by viewing the screen and judging the use of the instruments with the assistance of the video endoscope.

The surgical retractor comprises (a) two handles suitable for grasping positioned opposite each other and pivotally connected so that the handles move reciprocatingly relative to each other, (b) a head means connected to each handle so that each head means moves reciprocatingly relative to the other, (c) a means for locking the heads at a preset distance from each other, (d) each head means having a connector means suitable for connecting a blade, and (e) a blade connected to each head means through the connector means with each blade having a width, depth and thickness so that the width extends substantially parallel to the length of the head and the depth extending downward from the top of the head. The blades, when taken together at the position of closest proximity to each other are of a size suitable to be inserted into a surgical incision in a patient undergoing a surgical procedure then spread apart to form an elongated, ovoid access opening through which a medical instrument may be inserted to perform exploratory, diagnostic or surgical procedures.

Preferably, the surgical retractor is designed so that each blade has an inside face and an outside face. The inside face of each blade faces the inside face of the other blade and the outside face of each blade is designed to (i) minimize the trauma to the patient's body at the incision when the head means and blades are spread apart, (ii) stabilize the blades in the incision and (iii) allow customization for each patient's anatomy.

Referring now to FIGS. 10A–10D, one sees the adjustable surgical retractor useful in the invention generally designated as 102. The retractor is characterized by having a elongated handle 104R and 104L for the right and left side as shown in FIG. 10A. The elongated handles have a grasping end shown as 106L and 106R for the left and right sides of the device which are proximal to the user. On the opposite end, distal from the grasping handle are the ends 108L and 108R, again indicating the left and the right side as shown in the figure. Generally the ends 108L and 108R when in the closed position shown in FIG. 10A will be in contact and there will generally be a space between opposing jaws of the device 109L and 109R. The handles which are suitable for grasping and are positioned opposite to each other are pivotally connected at pivot point which will have a male member pivot pin 110 which will correspond to a female receiving member 111 to allow the pivoting to take place. Thus the opposite ends 108L and 108R that are distal to the grasping handles comprise heads that are connected to each elongated handle so that each head moves reciprocatingly relative to the other. When handles 106L and 106R are drawn together as shown in FIG. 10D, the distal ends or heads 108L and 108R are spread apart. A key to the utility of this particular design is the presence of a locking means to lock the heads at a preset distance from each other. The means shown in this case is a ratchet segment 114 having teeth 116 along the arcuate member 115 and interconnecting handles 104L and 104R. Working in concert with the ratchet segment 114 and its corresponding teeth 116 is a corresponding pawl member 118 which is pivotally mounted at pivot 119, not shown, working in concert so that the teeth 120 on pawl 118 (as shown in FIG. 10D) are complementary to the teeth 116 and provide a means for locking the heads at a preset distance from each other. Because of the numerous teeth 116 along ratchet member 114 the distance between head members 108L and 108R can vary significantly and in small incremental amounts. When pawl member 118 is disengaged from the ratchet segment 114 by not having the teeth in contact, tensioning means 112 tends to keep the handles 106L and 106R apart. Thus if the teeth are not engaged, the handles will tend to be spread apart by the tensioning means so that the heads 108L and 108R are generally in contact and ready for insertion prior to a surgical operation.

Each head means (which is shown as being unitary with the handle) has a connector means suitable for connecting a connector blade 122 to the corresponding heads 108L and 108R of elongated handles 104L and 104R. A blade 122 is connected to the head member of the elongated handle 104 by a connector means not shown, with each blade 122 having a width, depth and thickness dimensions that define the blade. The width, for purposes of this invention, is said to extend substantially parallel to the length of the head or handle. The top of the blade as seen as 123 in FIG. 10A such that while in use, the blade would be inserted into the surgical incision and the top edge 123 would remain outside the patient's surgical opening. The depth of the blade would extend downward from the top 123 of the blade into the surgical incision. Thus by looking at the side view of FIG. 10A along lines 10B–10B', the bottom of the blade 122 would be shown as 124 in FIG. 10B. The bottom of blades 124, when taken together at the position of closest proximity to each other as shown in FIG. 10A, are of a size suitable to be inserted into a surgical incision in a patient undergoing a surgical procedure. Once inserted, the blades are then spread apart as shown in FIG. 10D to form an elongated access opening through which a medical instrument may be inserted to perform diagnostic, exploratory or surgical procedures. The view of FIG. 10B of the surgical retractor of this device is a side view along lines 10B to 10B' in FIG. 1A while an end view along lines 10C to 10C' is shown in FIG. 10C. The numbers in each of FIGS. 10A–10D, all designate similar parts of the device.

In another aspect that enhances the doctor's ability to perform the surgery, a three-dimensional (3D) viewing monitor is provided. The 3D monitor aids the surgeon particularly when he is suturing in a process of anastomosis. Providing the 3D view aids him or her in performing the suturing techniques that are viewed with the assistance of the view scope and the monitor. It is found that for cardiac surgery a 3-D monitor that uses specialized glasses is preferable to a head-mounted display in that the resolution is better for the former than the latter. Turning now to FIG. 7, one can see a preferred aspect of the invention where the surgeon's vision is further enhanced with a 3D monitor as well as a flat panel 2D monitor. Here, the patient 74 is positioned on operating table 73 which has a flex arm 75 attached to it similar to the attachment shown in FIGS. 4A and 4B where the flex arm has the viewing monitor shown as a flat panel 76. Here, the flat panel is positioned it, close proximity to the patient so the doctor's line of vision provides him with visual reality of the work that he's doing internally. The view scope 78 is positioned to show the internal thoracic region of the patient and the doctor is able to manipulate instruments similar to that manner shown in FIG. 6. The doctor is provided with goggles 77 through which he can view the 3D monitor when he wants to have a three dimensional vision of the work he is doing surgically within the patient. Generally a 3D monitor and glasses is available from Automated Medical Products, 2315 Broadway, New York, N.Y. The vision glasses are referred to as "crystal eyes". Another source of the glasses is Crystal Eyes Stereographics, San Rafael, Calif. (Model CEPC). The vision goggles are designed so that when the head moves down, the 3D sensation is voided and the doctor can then look at the flat panel directly above the patient. The flat panel may be obtained from CTX Opto, Inc., Sunnyvale, Calif. (Part No. 95.53101.001) The surgeon's assistants 82 and 83 are available to assist and move the flex arm and flat panel 76 as well as the 3D monitor 80 as desired. The image from the view scope is provided to both the flat panel 76 as well as the three dimensional monitor 80 though the doctor is seeing exactly the same view in both cases.

Another aspect of this invention is the surgical drape that is suitable for covering the viewing screen. The drape is designed to allow the method of this invention to take place. Thus, the drape is designed to drape the viewing monitor with a transparent surgical sterile drape so that the viewing monitor can be placed within the surgical field as a sterile entity. Turning now to FIG. 8A, one sees a design for one aspect of a drape of this invention. The dray is shown generally as 86. It is shown to have a cruciform configuration having four arms 87, 88. 89 and 90, with arm 87. Extensions may also be present on the arms as desired for expanded and overlapping coverage. Around the periphery or near the periphery of each of the arms is a fastening means that allows the drape to encircle a viewing monitor. The arms are folded in a manner to enclose the viewing monitor and allow it to be placed within the surgical field without decreasing the sterility of the field. Generally, the drape will be folded and packaged in a sterile package for use in surrounding the viewing monitor and will be accompanied by instructions on how to enclose the monitor. Thus, around the periphery of the drape 86 will be fastening means. Here, they are shown as being Velcro hook and loop fasteners. The fastening means will be placed around the periphery of the drape, e.g. on the surfaces of the arms in a manner that allows the arms to be folded and interlocked, thus, enclosing the viewing monitor. The shape of the sterile drape will vary depending on the shape of the monitor. The drape that is shown in FIG. 8A is suitable for a flat panel monitor. Here, the Velcro hook and loop fastener pad 92 of arm 87 is placed on the surface of the drape that is opposite the viewer of FIG. 8A. The interacting Velcro hook and loop fastener 96 on the other side is placed on the surface of the arm 89 of the drape that is toward the viewer. This is shown as 96 on arm 89. On arm 89, there is also shown a slight gap having interlocking pieces of Velcro hook and loop fasteners 95 and 97 on opposite faces of the arm 89 so that the cord 99 as shown in FIG. 8B can go through the arm 89. Turning to FIG. 8B, one sees a flat panel monitor 91 being partially enclosed by the sterile drape 86. Here, the arm 87 is folded over the top of the flat panel 91 and positioned with the arm going down and arm 89 having the interacting Velcro hook and loop fastener 96 then fits so that the Velcro hook and loop fastener pieces fasten together and maintain the transparent sterile drape firmly across the viewing screen of the flat panel. The cord 99 of the flat panel 91 is shown as coming out between the back of panel 91 and flap 89. Before 87 and 89 and 95 and 97 are firmly engaged, the adhesive 93, which is on the surface of drape 86 is contacted with the surface of the viewing screen of 91 to firmly position the drape so that the viewing screen is clearly visible. Once arms 87 and 89 are in place, the other arms 90 and 88 are folded in the direction of the arrows shown so that the Velcro hook and loop fastener which is shown as 98 on arm 90 and is on the opposite face from the viewer interacts with Velcro hook and loop fastener 94 on arm 88 to completely enfold the monitor 91.

Alternatively, the flexible drape may be configured as a sleeve designed to receive a viewing monitor (particularly a flat panel monitor) and having a closable flap to ensure sterility of the monitor. This can be seen in FIGS. 9A and 9B.

Here we can see a flat panel viewing monitor shown generally as 160 and having a screen 161 for viewing. The flat panel is designed to fit into sterile enclosure 162 in the direction of the arrows. The sterile enclosure has a front panel 164 that is transparent so that the screen 161 can be clearly seen through the transparent front panel. It has a side panel 166 which ensures a snug fit of the flat panel into the enclosure. In the rear of the enclosure 167 there is an opening 169 that provides an access for the power cord and/or the transmission cord from the processing unit. Once the flat panel is snugly fitted within the sterile enclosure the top flap 168 is folded over in the direction of the arrows shown to enclose the flat panel and assure its sterility. Around the perimeter of the edge of the panel the flap 168 is a tracking of Velcro hook and loop fastener 170. This Velcro hook and loop fastener will interact with the other Velcro hook and loop fastener 171 on the outside of the enclosure to ensure that the flat panel will be fully enclosed within the sterile enclosure. Once the flat panel is in the sterile enclosure, the cord can be inserted at the back of the panel 167 through opening 169 and the cord can also be covered with a sterile drape by fitting it around the cord so that the viewing monitor can be positioned within the surgical field in accordance with the method of this invention as discussed hereinbefore.

In a preferred embodiment a stiff frame is placed either in sleeve 162 on the inside of face 164 or is adhered to the front face of monitor 160 to ensure the transparent drape is drawn taut to minimize distortions in the transmission of the image on screen 161 through the drape. If placed inside the sleeve it is positioned firmly against the inside of front panel 164 and the panel 164 is pulled tightly around the frame. If adhered to the adhesive strips (unnumbered). around screen 161 of monitor 160, the outside perimeter of the frame is slightly larger than the face of monitor 160, again to insure tightness of the drape.

Another aspect of the invention is an endoscopic visualization apparatus. This apparatus comprises a view scope having a light source, camera and lens means, where the view scope has the lens means positioned in a nose piece designed to be inserted percutaneously into a patient's internal cavity to gather and transmit an image from the distal end of the lens means to the camera. Associated with the view scope is the signal transmission cord from the camera to a signal processing unit, C.P. on interface. In addition, there is a power transmission cord for each of the light source camera and signal processing unit to plug into a power source. The signal processing unit is capable of interpreting the signal from the camera and transmitting a further signal to a viewing monitor through a signal transmission cord. The view monitor is capable of exhibiting the image gathered from the patient's internal cavity on a screen portion of the viewing monitor. The unique aspect of the apparatus is the positioning ,of the camera at about a 90° angle relative to the nosepiece to minimize the distance that the view scope extends out of the patient. This is particularly important for a surgeon for performing closed-chest surgery because it allows the surgeon to get significantly closer to the patient when performing the surgery. Generally, a surgeon will be away from the patient a distance of about 12–24" using the view scope of the presently available products. By the design of this particular apparatus, the surgeon can get within less than 6" of the patient, generally less than 5" and preferably less than 2". This is achieved by using a prism or mirrors to provide a 90° angle of the camera relative to the nosepiece where the lens and light source go into the patient.

The unique aspects of the view scope of this invention may be seen in FIGS. 12A and 12B. The view scope is generally comprised of a light source and lens carried in nosepiece 67 and a camera 66. Viewing the detailed end and view of FIG. 12B one sees the light source or port for providing light to the area being viewed. Also one sees the lens means or viewing port 162. Optionally, lumens 163 and 164 are provided to transport fluids to and from the area being observed. The light bundle 160 is attached as shown externally. The camera is placed at about a 90° angle relative to nosepiece 67. This is accomplished by using mirror 165 to deflect the image along lens means 162 to cameral 66.

Other optional and preferred characteristics of the view scope include a zoom capability for the lens means and a motion sensor to maintain alignment of the view scope to maintain the surgeon's sense of visual reality.

Turning now to FIG. 11, one can see a diagrammatic view of the various components that are useful in the apparatus of this invention. Number 130 generally shows the view scope which comprises the camera 132, the light source 134, along with light transmission line 133, going to nosepiece 136 which also contains the lens which is used to gather the image internally and transmit it back to the camera along transmission line 138. Once the image is transmitted to camera 132, it is further transmitted along transmission line 140 to a signal processing unit 142 which interfaces with the viewing monitor 144, having a screen 145 on which the image is exhibited. The nosepiece 136 will have an end 135 that is distal from the camera and an end 137 that is proximal to the camera. Each of the light source, camera and the signal processing unit have power cords 139, 141 and 143 leading to a power source 146. The signal processing unit 142 transmits a signal to the viewing monitor 144 and the image gathered at the distal end 135 of nosepiece 136 of view scope 130 is exhibited on the screen 145. As pointed out previously, it is preferable that the viewing monitor is a flat screen monitor which fits into the surgical field more readily than a larger regular television monitor. Preferably, the apparatus set forth above is associated with a movable cabinet in which the power source, the signal processing unit and the flat screen monitor are located. The movable cabinet will have an adjustable arm which has a distal end a proximal end relative to the cabinet. The flat screen viewing monitor will be attached to a platform at the distal end of the adjustable arm. In this manner, the screen can be draped with a sterile drape in accordance with the invention and positioned into the surgical field to aid the surgeon in performing the internal video-assisted surgery. This can be seen in FIG. 5, showing the cabinet 44 and the adjustable arm 42 as discussed hereinbefore. In a preferred embodiment, the apparatus also includes a 3D signal processing unit, shown as 148, along with a three-dimensional viewing monitor 150, a three-dimensional viewing goggle control emitter 152 and the corresponding 3D viewing goggles 154. Leading to the 3D signal processing unit 148 is the transmission cord 147. The signal processing unit 148 is connected to the three-dimensional viewing monitor 150 through transmission cord 149. The viewing goggle control emitter 152 is connected to the 3D processing unit through cord 151. The three-dimensional signal processing unit and the three-dimensional viewing monitor are connected to a power source through cords 153 and 155, respectively. The arrangement for the operation of the apparatus can be seen generally in FIG. 7. Referring, however, to FIG. 11, from an operational standpoint the view scope is inserted percutaneously into the patient to view an internal region to be operated on, for example, the thoracic region. The image is lighted by the light source and transmission line 134 and 133 and transmitted to the camera and the flat screen 2D monitor through the flat screen interface 142 and to the 3D monitor 150 through the three-dimensional signal processing unit 148. The flat screen monitor is positioned into the surgical field similarly to that position shown in FIG. 7 and the 3D monitor is positioned to be in line with the surgeon's direct view of the flat panel within the surgical field and the 3D monitor. The surgeon wears viewing goggles 154 and when he views the 3D monitor directly, the emitter activates the viewing goggles so that he can see the image in three dimensions as he is doing the operation. This is particularly valuable to the surgeon to the suturing of, for example, the internal mammary artery to the left descending coronary artery. When the surgeon wishes to look down at the flat panel, he shifts the viewing goggles to be outside of the range of the control emitter and is able to see the internal view on the flat panel within the surgical field to give him a sense of visual reality.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. In a method for a closed chest, video-assisted diagnostic or surgical treatment of a patient that comprises positioning a viewing scope having an elongated nosepiece suitable for gathering and transmitting images to a small video camera so that the nosepiece is inserted through a first percutaneous intercostal opening in the patient to view an internal region of the patient requiring diagnostic or surgical treatment and transmitting the image so gathered through the video camera to a viewing monitor, providing at least a second percutaneous opening suitable for inserting a surgical or diagnostic instrument therethrough, inserting a first diagnostic or surgical instrument through said second opening to perform an internal diagnostic or surgical procedure in the patient's cavity while viewing the image of said procedure on the monitor, the improvement that comprises (a) draping said monitor with a transparent, sterile surgical drape, said drape completely covering said monitor and being fastened around a periphery of a screen of said monitor, and (b) positioning said draped monitor within a surgical field so that the surgeon can perform the internal surgical or diagnostic procedure and view it on said monitor so that the surgeon's visual access to the monitor correlates as closely as possible to the visual access of an input end of the viewing scope.

2. The improvement of claim 1, wherein the monitor is a flat panel monitor.

3. The improvement of claim 1, wherein said draped monitor is on a movable cart having a sterilizable adjustable arm that allows the monitor to be positioned within the surgical field and adjusted to enhance the surgeon's visual alignment.

4. The improvement of claim 1, wherein the closed-chest surgical treatment of the patient is performed on an operating table having a means to hold the viewing monitor within the surgical field and adjust the position of the viewing monitor within the surgical field to enhance the surgeon's visual alignment.

5. The improvement of claim 4, wherein said means to hold the viewing monitor is a flexible, adjustable arm having a proximal and distal ends, said proximal end connected to the operating table and said distal end having a means for firmly holding said viewing monitor in place.

6. The improvement of claim 1, wherein the video camera of said viewing scope is positioned at about a 90° angle relative to said elongated nosepiece to enable the surgeon to maximize proximity to the patient in performing the surgical treatment.

7. The improvement of claim 1, wherein the drape is connected to the viewing monitor, thereby ensuring a high resolution image.

8. The improvement of claim 7, wherein the drape is connected to the viewing monitor by adhesive.

9. The improvement of claim 8, wherein the adhesive connects the drape to the monitor adjacent to the screen.

10. The improvement of claim 7, wherein a portion of the drape covering a screen of the monitor is pulled taut.

11. The improvement of claim 1 wherein a surgical retractor provides percutaneous access for the insertion of the surgical or diagnostic instrument into the patient's internal region, said retractor comprising
    (a) two handles suitable for grasping positioned opposite each other and pivotally connected so that the handles move reciprocatingly relative to each other,
    (b) a head means connected to each handle so that each head means moves reciprocatingly relative to the other,
    (c) a means for locking the heads at a present distance from each other,
    (d) each head means having a connector means suitable for connecting a blade, and
    (e) a blade connected to each head means through the connector means with each blade having a width, depth and thickness.

12. The improvement of claim 11 wherein the surgical retractor is designed so that each blade has an inside face and an outside face, with the inside face of each blade facing the inside face of the other blade and the outside face of each blade is designed to (i) minimize the trauma to the patient's body at the incision when the head means and blades are spread apart, (ii) stabilize the blades in the incision and (iii) allow customization for each patient's anatomy.

13. A flexible sterile drape for covering a video monitor within a surgical field of a surgical operation to be performed on a patient, which drape comprises a window formed of a transparent material within a perimeter of the drape and positioned to cover a screen of said monitor, and fastening means around the perimeter of the drape for completely covering the video monitor to ensure the monitor's sterility and suitability for retaining within a surgical field during a surgical operation on a patient and for fastening said drape around a periphery of said screen.

14. The sterile drape of claim 13, wherein the entire drape is transparent.

15. The sterile drape of claim 13, that is packaged in a sterile package.

16. The sterile drape of claim 13, wherein the fastening means includes adhesive strips.

17. The sterile drape of claim 13, that is made of polyethylene or polypropylene.

18. The sterile drape of claim 13, wherein the fastening means includes hook and loop fasteners.

19. The sterile drape of claim 13, wherein the fastening means includes snaps.

20. The sterile drape of claim 13, further comprising a sterile package in combination with instructions for enclosing a viewing monitor.

21. The improvement of claim 13, wherein a portion of the drape covering a screen of the monitor is pulled taut.

22. A flexible sterile drape for covering a video monitor located within a surgical field of a surgical operation, the drape comprising:
    a drape body configured to completely cover a video monitor,
    a transparent viewing window of transparent material located within the drape body, and
    a fastener configured to connect the drape body to the video monitor around a perimeter of a screen of the video monitor.

23. The flexible drape of claim 22, wherein said drape body has a cruciform shape.

24. The flexible drape of claim 22, wherein the fastener is a plurality of segments of hook and loop fastener.

25. The flexible drape of claim 22, wherein the fastener is adhesive.

26. The flexible drape of claim 22, used in combination with the video monitor.

27. The flexible drape of claim 22, wherein the drape is packaged in a sterile package combined with instructions for enclosing a viewing monitor.

* * * * *